United States Patent [19]

Kobayashi et al.

[11] Patent Number: 4,909,986
[45] Date of Patent: Mar. 20, 1990

[54] AQUEOUS DEODORANTS AND DEODORIZING METHODS

[75] Inventors: Nobuo Kobayashi; Azuma Kawazoe, both of Tokyo, Japan

[73] Assignee: Dainippon Ink, Tokyo, Japan

[21] Appl. No.: 887,358

[22] Filed: Jul. 21, 1986

[30] Foreign Application Priority Data

Jul. 23, 1985 [JP] Japan ................................ 60-161204
Jul. 23, 1985 [JP] Japan ................................ 60-161205

[51] Int. Cl.$^4$ ........................... A61L 9/01; A61L 9/14
[52] U.S. Cl. ........................................... 422/4; 422/5; 424/76.2; 424/76.21; 424/76.3
[58] Field of Search ...................... 424/76, 76.2, 76.3, 424/76.21; 422/5, 4

[56] References Cited

U.S. PATENT DOCUMENTS

| | | | |
|---|---|---|---|
| 2,754,245 | 7/1956 | Hosmer | 422/5 X |
| 2,930,768 | 3/1960 | Hopkins | 424/76 X |
| 3,250,724 | 5/1966 | Kulka | 422/5 X |
| 3,567,119 | 3/1971 | Wilbert et al. | 424/76 X |
| 3,655,569 | 4/1972 | Hellsten et al. | 252/99 |
| 3,966,902 | 6/1976 | Chromocek | 424/76 X |
| 4,154,817 | 5/1979 | Tsuchiya et al. | 424/76 |
| 4,415,551 | 11/1983 | Fang | 424/78 X |
| 4,517,333 | 5/1985 | Lundberg et al. | 524/516 |

FOREIGN PATENT DOCUMENTS

| | | |
|---|---|---|
| 157834 | 12/1979 | Japan . |
| 160737 | 12/1979 | Japan . |
| 2002227 | 2/1979 | United Kingdom . |
| 2038183 | 7/1980 | United Kingdom ..................... 422/5 |

Primary Examiner—Barry S. Richman
Assistant Examiner—Jill Johnston
Attorney, Agent, or Firm—Sherman and Shalloway

[57] ABSTRACT

A deodorant comprising as essential components [I] a water-soluble organic polymer having a number average molecular weight of at least 100,000 and containing at least one group selected from the class consisting of a carboxyl group and its ammonium salt, ammonium/alkali metal mixed salts and alkanolamine salts; sulfoalkyl groups, a sulfonic acid group, a phosphoric acid group, and a phosphonic acid group and their alkali metal salts, ammonium salts, alkanolamine salts and alkali metal-/ammonium/alkanolamine mixed salts; and cationic groups, and/or a quaternary ammonium compound of the polymer, and [II] an aqueous medium.

18 Claims, No Drawings

AQUEOUS DEODORANTS AND DEODORIZING METHODS

This invention relates to a range of aqueous deodorants which exhibit a marked deodorizing effect over long periods of time on various substances which are physiologically toxic or unpleasant malodorous sources.

Physiologically toxic or unpleasant malodors occur widely in the living environments of man, for example in the production, processing, repacking, filling, storing, freshness retaining, transportation, discarding, etc. of various products typically of industry, agriculture, forestry, animal husbandry husbandly and fishing. There are a large variety of substances which cause such malodors, but in many cases, the main components of these are organic and/or inorganic compounds having a molecular weight of less than several hundred, for example sulfurcontaining compounds such as sulfur dioxide, hydrogen sulfide, mercaptans and alkylsulfides, ammonia, nitrogen oxides represented by $N_xO_y$ (where both x and y are integers), amines such as methylamines, aldehydes, mercaptans, indoles such as indole and skatole (methylindole), and peptones.

The following measures have been taken for controlling such various physiologically toxic and unpleasant malodor-causing substances.

(1) Utilization of the masking action of a third substance for the purpose of changing the nature of smells, or alleviating or reducing the smells. Examples of such a third substance are naphthalene, p-dichlorobenzene, camphor oil, citronella oil, lemon oil, turpentine oil, essential oils and perfumes.

(2) Utilization of an offsetting action whereby two or more different smells are mixed in specific proportions to make the malodors unperceptible by man. For example, a combination of musk and almond, a combination of skatole and coumarin and a combination of ethylmercaptan and may be utilized.

(3) Utilization of adsorbents such as activated carbon or silica gel.

(4) Utilization of a chemical deodorizing method on sources of sulfur-containing malodors, for example a toilet tank additive comprising a combination of ferrous sulfate and ascorbic acid.

(5) Use of a household aerosol comprising an aqueous solution of a combination of lauryl methacrylate, o-phenyl phenol, geraniol or crotonate with citric acid or malic acid sealed in a metal container together with Freon, dimethyl ether, propane or butane.

(6) A method which comprises washing malodorous air with water and then discharging the clean air.

The method based on the use of an adsorbent such as activated carbon is effective only to some extent unless used in a closed system, and has a short effective life.

The chemical deodorizing method using ferrous sulfate has the defect that when ferrous sulfate changes to ferric sulfate, an article to be treated (such as an apparel) is discolored and the types of malodor-causing substances to which it be effectively applied are limited.

The method of masking malodors using perfumes having strong fragrance has the disadvantage that since the components of the perfumes have odors, they cannot exhibit a sufficient deodorizing effect on ammonia, hydrogen sulfide and mercaptans.

One of the present inventors already discovered deodorants which are not perfumed, have high versatility and no discoloration, and show a long-lasting deodorizing effect on a broad range of malodorous substances. Such deodorants were proposed in Japanese Laid-Open Patent Publication No. 160737/1979 as "a liquid deodorant comprising an aqueous medium and polyacrylamide as an active component", and Japanese Laid-Open Patent Publication No. 157834/1979 as "a liquid deodorant comprising poly(sodium acrylate) as an active component". The specifications of these patent publications state that the deodorizing effects of these deodorants are increased by using sodium acrylate/acrylamide copolymer in combination.

It is an object of this invention to provide a deodorant which is applicable to a much wider range of malodor-causing substances than the deodorants disclosed in the above-cited Japanese patent documents, and has resistance to fermentative decomposition by bacteria or enzymes and durability of the effect.

According to this invention, there is provided a deodorant comprising as essential components [I] a water-soluble organic polymer having a number average molecular weight of at least 100,000 and containing at least one group selected from the class consisting of a carboxyl group and its ammonium salt, ammonium/alkali metal mixed salts and alkanolamine salts; sulfoalkyl groups, a sulfonic acid group, a phosphoric acid group, and a phosphonic acid group and their alkali metal salts, ammonium salts, alkanolamine salts and alkali metal-/ammonium/alkanolamine mixed salts; and cationic groups or a quaternary ammonium compound of the polymer, and [II] an aqueous medium; and a method of deodorization, which comprises spraying the deodorant into a flowing or nonflowing gas, spraying it to the surface of a solid or liquid, impregnating it into a porous material, or incorporating it into a powder or a gel-like substrate.

According to this invention, there are also provided an aqueous deodorant comprising as essential components a water-soluble organic polymer having a number average molecular weight of at least 100,000 and containing at least one group selected from the class consisting of an amide group, an imide group, a carboxyl group, a sulfonic acid group, sulfoalkyl groups, a phosphoric acid group and a phosphonic acid group, alkali salts thereof, and cationic groups, and/or its quaternary ammonium compound, and at least one material selected from (a) a water-soluble organic polybasic acid having not more than 15 carbon atoms and/or a salt thereof, (b) an organic monobasic acid and a salt thereof, (c) a water-soluble carbonate and/or bicarbonate, (d) a water-soluble oxoacid salt of sulfur, (e) a water-soluble alkanolamine or aqueous ammonia, (f) a mixture of iodine pentoxide and sulfur, (g) a water-soluble natural polymer, and (h) an alkali metal hypochlorite and a derivative thereof; and a method of deodorization which comprises spraying the deodorant into flowing or non-flowing gas, spraying it on the surface of a solid or liquid, impregnating it into a porous material, or mixing it with a powder or a gel-like substrate.

The nonionic, anionic, cationic or amphoteric water-soluble organic polymer having a number average molecular weight of at least 100,000 and containing at least one of an amide group; an imide group; a carboxyl group or an ammonium salt, ammonium/alkali metal mixed salt or alkanolamine salt thereof; a sulfomethyl group, a sulfonic acid group, a phosphoric acid group and/or a phosphonic acid group or an alkali metal salt, an ammonium salt, an alkanolamine salt and/or a mixed salt of these groups; and cationic groups is a polymer or copolymer derived from the following monomers or a mixture of such polymer or copolymer.

(1) Examples of ethylenically unsaturated monomers having an amide or imide group Acrylic monomers having not more than 12 carbon atoms, for example acrylamide, methacrylamide [the two will be inclusively referred to as (meth)acrylamide], monoalkylated (meth)acrylamide, alkylenebis(meth)acrylamide (the alkylene group preferably has not more than 4 carbon atoms, and may be partly replaced by the OH group), and diacetone (meth)acrylamide.

(2) Examples of monomers containing a polymerizable unsaturated group bearing a carboxyl group (giving anionic property)

Monomers having a polymerizable unsaturated group and not more than 8 carbon atoms such as acrylic acid, methacrylic acid, crotonic acid, 2-(meth)acryloyloxyethylsuccinic acid, 2-(meth)acryloyloxyethylphthalic acid and 2-(meth)acryloyloxyhydrophthalic acid.

(3) Examples of monomers having a polymerizable unsaturated group with a sulfonic acid group, a sulfoalkyl group (preferably 2 or 3 carbons), a phosphoric acid group or a phosphonic acid group (giving anionic property)

Monomers containing a sulfonic acid group, a sulfoalkyl group or a phosphonic acid group having not more than 10 carbon atoms such as vinylsulfonic acid, mono[2-(meth)acryloyloxyethyl]acid phosphate, sulfoethyl (meth)acrylate, sulfopropyl methacrylate, 2-(meth)acrylamide-2-methylpropanesulfonic acid, ethylenesulfonic acid, and vinylphosphonic acid.

(4) Examples of monomers having cationic groups (giving cationic property)

Monomers having cationic groups having not more than 15 carbon atoms such as dimethylaminoethyl (meth)acrylate, dimethylaminopropyl (meth)acrylate, diallyldimethylamine, diallyldiethylamine, vinylbenzyldimethylamine, and N-t-butylaminoethyl (meth)acrylate.

(5) Examples of monomers having a polymerizable unsaturated group and a quaternary ammonium salt structure (giving strong cationic property)

Monomers having a quaternary ammonium salt structure obtained by reacting the aforesaid monomers (4) having cationic groups with at least one inorganic or organic acid such as hydrochloric acid, sulfuric acid, phosphoric acid, succinic acid, malonic acid, DL-malic acid, ascorbic acid, borogluconic acid, galactogluconic acid, gluconic acid, citric acid, iso-valeric acid, lactic acid, phosphorylated lactic acid, levulinic acid and propionic acid. Typical examples include 2-(meth)acryloyloxyethyl trimethyl ammonium chloride, 2-hydroxy-3-(meth)acryloyloxypropyl trimethyl ammonium chloride, diallyl dimethyl ammonium chloride, vinyl benzyl trimethyl ammonium chloride, and sulfites of these.

(6) Other copolymerizable nonionic monomers may be used as copolymer components together with (1), (2), (3), (4) and (5).

In addition to (co)polymers comprising at least one of the monomers (1), (2), (3), (4) and (5) and the copolymers (6), the following (co)polymers and their modified products may be cited.

(7) Polymers having an ammonium salt structure formed by adding the inorganic or organic acids shown in (5) above or other inorganic or organic acids to aqueous solutions of cationic polymers, cationic copolymers or amphoteric copolymers composed of or comprising the cationic monomers (4) to quaternize them.

(8) Cationic or amphoteric polymers obtained by subjecting nonionic or anionic polymers or copolymers (as exceptions, cationic or amphoteric copolymers) composed of or comprising the monomers (1) to a Mannich reaction, known as a method of introducing a cationic group, whereby formaldehyde is reacted with a primary amine or preferably a secondary amine having not more than 5 carbon atoms in the alkyl moiety, such as dimethylamine as shown by the following scheme:

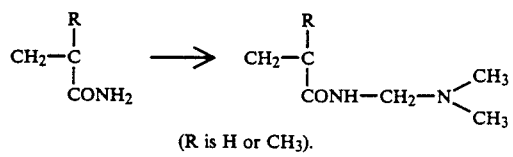

(R is H or CH₃).

This method is easiest and most economical for the production of cationic or amphoteric polymers or copolymers.

(9) Polymers obtained by modifying the cationic or amphoteric (co)polymers of (8) so as to have a quaternary ammonium salt as in (7) above.

(10) Polymers obtained by introducing an anionic group into nonionic or cationic (as exceptions, anionic or amphoteric) copolymers comprising acrylamide or methacrylamide as a main constituent monomer by reacting formaldehyde and a bisulfite ion ($S_2O_4^-$) thereby to introduce a sulfomethylated group.

(11) Monomers capable of constituting other water-soluble organic polymers, such as vinyl pyrrolidone, polyethylene glycol mono(meth)acrylate (molecular weight not more than 4,000), and polypropylene glycol mono(meth)acrylate (molecular weight not more than 4,000), glycerol mono(meth)acrylate.

The monomers having acidic groups such as (2) and (3) may be used as such or in the form of salts with alkali metals, ammonium, and/or alkanolamine groups having not more than 10 carbon atoms, such as 2-amino-2-methy-1-propanol. Neutralization with the alkaline substance may be carried out at any stage before or after polymerization. Or it may not be carried out at all.

Examples of the method of producing water-soluble organic polymer as an essential component in this invention are given below.

(1) Process of producing water-soluble organic polymers

The cationic, anionic or amphoteric polymer used in this invention can be produced by methods as shown below.

(i) A monomer such as (meth)acrylamide, and/or cationic monomers and/or anionic monomers to be described below are free-radically (co)polymerized usually in water either alone or as a mixture. In this case, the number average molecular weight of the polymer should be adjusted to at least 100,000, preferably 1,000,000 [a method of producing a nonionic (meth)acrylamide polymer which is used as the intermediate and of producing anionic, cationic and amphoteric polymers].

(ii) An alkali such as sodium hydroxide or an acid is added to the polymer composed only of (meth)acrylamide obtained by the method (i) to hydrolyze the polymer partly or wholly. Alternatively, the polymer is first converted to its complete or partial salt, and a small quantity of strong acid such as hydrochloric acid and then ammonia and/or an alkanolamine such as 2-methyl-2-amino-1-propanol are added to the alkali salt to produce an ammonium salt of the polymer or an alkali metal/ammonium mixed salt of the polymer. [Method of producing anionic polymers]

(iii) When the polymer obtained by the method (i) is produced by copolymerizing (meth)acrylamide with a carboxyl group-containing monomer or a polymer composed of a monomer containing only acidic groups, it is neutralized with ammonia and/or an alkanolamine or a mixture thereof with an alkali metal hydroxide (a method of producing anionic polymers).

(iv) When the polymer obtained by the method (i) is a water-soluble copolymer of (meth)acrylamide and monomers containing such acid groups, a sulfonic acid group and/or a phosphoric acid group and/or a phosphonic acid group, it is used without neutralization or after being neutralized with an alkali metal hydroxide. Preferably, it is neutralized with an aqueous solution of ammonia and/or an alkanolamine or neutralized so that it is converted to an ammonium/alkali metal mixed salt or an alkanolamine/alkali metal mixed salt. (Method of producing anionic polymers)

(v) When the polymer obtained by the method (i) is polymer comprising cationic monomers or a copolymer containing a cationic monomer, the tertiary amino group of the polymer or copolymer is reacted with an acid such as hydrochloric acid to convert it to a quaternary ammonium salt, thereby imparting stronger cationic property (cationic polymer).

(vi) When the polymer obtained by the method (i) is obtained by the polymerization or copolymerization of (meth)acrylamide, it is reacted with formaldehyde and a secondary amine having not more than 8 carbon atoms in total, such as dimethylamine (known as the Mannich reaction) to form a dimethylamino-N-methyl(meth)acrylamide polymer. As required, a quaternary ammonium salt structure is formed as mentioned in the method (v). (Production of cationic polymers)

(vii) The (meth)acrylamide polymer or copolymer obtained by the method (i) is wholly or partially sulfomethylated by reacting it with formaldehyde and bisulfite ions ($S_2O_4^-$) or a salt thereof (a method of producing anionic polymers).

(viii) Amphoteric polymers may be produced by copolymerizing an anionic monomer and a cationic monomer with or without adding acrylamide; rendering the amide groups of the anionic copolymers obtained by the methods (i), (ii), (iii), (iv) and (vii) cationic by the Mannich reaction in (vi); or by partially hydrolyzing the amide group of the cationic copolymers obtained by the method(v) and (vi) (production of amphoteric polymers).

The (co)polymers obtained by various methods may be used singly or two or more of them may be used as a mixture so long as they are not coagulated. They may also be mixed with polyacrylamide, poly(sodium acrylate) or other water-soluble polymeric compounds.

The water-soluble organic polymer used in this invention, contains 5 to 95% by weight of the (meth)acrylamide component, and has a number average molecular weight of at least 100,000. If the average molecular weight is less than 100,000, the deodorizing effect of the polymer is low. Water-soluble organic polymers having a number average molecular weight of at least 1,000,000 give favorable results. The level of the number average molecular weight can be easily determined by measuring the viscosity of the polymer by means of a Brookfield viscometer with a rotor No. 2 (#2 SPINDLE) using a 1% aqueous solution of the polymer at 20° C. at a rotor rotating speed of 60 rpm. Water-soluble organic polymers which are neutral and have a viscosity of not more than 100 centipoises roughly have a number average molecular weight of less than 100,000, and their deodorizing effect is small. Those having a viscosity of not more than 1000 centipoises have a fairly good deodorizing effect. Viscosities of at least 1000 centipoises roughly correspond to number average molecular weights of at least 1,000,000. Those having a viscosity of at least 3,000 centipoises show a very superior deodorizing effect.

Of course, the accurate molecular weight of the polymers can be measured in a customary manner. When the water-soluble polymer is a copolymer, there are many factors of viscosity variations, and the intrinsic viscosity method cannot be applied directly to the copolymer. In this case, the following method must be used. The copolymer is hydrolyzed with an alkali to poly(meth)acrylic acid or another polyacid without involving decomposition of the polymer, and thereafter, the hydrolyzed polymer is methy-esterified with diazomethane. The intrinsic viscosity of the methyl ester is then measured, and the molecular weight is calculated on the basis of the intrinsic viscosity.

Table 1 below shows specific examples of typical water-soluble organic polymers of used in this invention.

TABLE 1

| No. | Monomer composition | Weight ratio | Ionic property | Number average molecular weight |
|---|---|---|---|---|
| 1 | Dimethylaminoethyl acrylate | (100) | Strongly cationic | about 6,000,000 |
| 2 | Dimethylaminoethyl acrylate/ acrylamide | (50/50) | Moderately cationic | about 5,000,000 |
| 3 | Vinylbenzyl trimethyl ammonium chloride/acrylamide | (5/95) | Weakly cationic | about 3,000,000 |
| 4 | Ammonium acrylate | (100) | Moderately anionic | about 5,000,000 |
| 5 | ammonium styrenesulfonate/ acrylamide | (5/95) | Moderately anionic | about 2,000,000 |
| 6 | Ammonium acrylate/acrylamide | (15/85) | Weakly anionic | about 8,000,000 |
| 7 | Acrylamide/dimethylaminoethyl methacrylate/vinylsulfonic acid | (70/20/10) | Amphoteric | about 600,000 |
| 8 | Acrylamide/diethylaminoethyl acrylate/styrenesulfonic acid | (85/10/5) | Amphoteric | about 1,500,000 |
| 9 | Aulfomethylacrylamide/acrylamide | (20/80) | Moderately anionic | about 8,000,000 |
| 10 | Sulfomethylacrylamide/dimethyl | (20/20/60) | Amphoteric | about 8,000,000 |

TABLE 1-continued

| No. | Monomer composition | Weight ratio | Ionic property | Number average molecular weight |
|---|---|---|---|---|
| | amino-N—methylacrylamide/acrylamide | | | |

In the methods described in the above-cited Japanese Laid-Open Patent Publications, the polymeric compounds used are nonionic or anionic. For example, nonionic polyacrylamide having a number average molecular weight of about 8,000,000 shows a considerably high deodorizing effect on some kinds of malodor-causing substances, but in many cases, their deodorizing effects are limited, and complete deodorization cannot be achieved. Poly(sodium acrylate) in usual form of use has a low deodorizing effect on many malodorous substances or malodorous gases except on acidic gases such as hydrogen chloride gas or nitrogen oxides because it has low coagulating power. Anionic copolymers of acrylamide and ammonium acrylate in a weight ratio of 95–80/5–20 having a molecular weight of 8,000,000 show a considerably improved deodorizing effect on malodorous substances having cationic charges such as skatole, ammonia and methylamine than the above nonionic polyacrylamide, but have only an insufficient deodorizing effect on anionic malodorous substances such as hydrogen sulfide, sodium bisulfite, ammonium sulfite, hydrogen chloride gas, fatty acids, phenols and methyl disulfide. It has been determined by the present inventors that cationic polymers show especially good deodorizing effects on such anionic malodorous substances. Amphoteric polymeric compounds show a much better deodorizing effect than, or in other words about 2 to 3 times on an average as good as, nonionic polymeric deodorants on not only these anionic or cationic malodorous substances but also on most of other malodorous substances including styrene, acetylene, mercaptans, aldehydes, noninic malodorous substances, fecal odors and putrefying odors.

However, even when amphoteric polymeric compounds which have the best deodorizing effect, are versatile and have high flocculating ability are used, it is difficult to obtain a deodorizing efficiency of 100%, and the deodorizing efficiency is generally 70 to 90% at the highest. By using these various polymeric compounds in combination with various water-soluble additives having low toxicity and applying the mixtures in aqueous form, a deodorizing effect of nearly 100% can be obtained.

Substances which are added as essential components to the water-soluble organic polymers in this invention are shown below.

(a) Water-soluble organic polybasic acids having not more than 15 carbon atoms and salts thereof:

Nontoxic organic polybasic acids used in carbonated drinks, such as succinic acid, citric acid, tartaric acid and DL-malic acid, are preferred. In some applications, other dibasic acids such as oxalic acid, itaconic acid, sebacic acid, dodecanedioic acid, maleic acid, fumaric acid, glycerophosphoric acid and malonic acid can also be used. Water-soluble salts of these acids, for example their alkali metal salts, calcium salts, ammonium salts and alkanol ($C_{12}$ or lower)amine salts, may also be used.

(b) Organic monobasic acids and salts thereof

These are water-soluble low-toxic organic monobasic acids which are odorless or non-malodorous. Examples include benzoic acid, borogluconic acid, carbamic acid, hippuric acid, isovaleric acid, lactic acid, lactophosphoric acid, levulinic acid, methionic acid, pantothenic acid, phenolsulfonic acid, propionic acid, salicyclic acid, carbamic acid and ascorbic acid. Their salts include the alkali metal salts, calcium salts, iron salts, ammonium salts and alkanol($C_{12}$ or lower)alkanolamine salts.

It is noteworthy that when these odorless low-toxic organic acids (a) or (b) are added in the form of alkali metal salts or calcium salts under weak acidity to an aqueous solution of the water-soluble organic polymer used in this invention rather than using them directly, there is an outstanding improvement in deodorizing effects on malodors from acidic gases such as hydrochloric acid, sulfuric acid, nitric acid and hydrogen sulfide, putrefying odors of proteins, and malodors from animal excretions, and the durability of the deodorizing effects is also improved. The amounts of these substances to be added to the water-soluble organic polymer may be determined depending upon the concentration of a malodorous gas generated.

(c) Water-soluble carbonates and/or bicarbonates

Carbonates and/or bicarbonates of alkali metals, ammonium and/or alkanolamines having not more than 12 carbon atoms can be used.

(d) Water-soluble oxoacid salts of sulfur

For the direct purpose of deodorization, thiosulfates, bisulfates, persulfates, pyrosulfates, acidic sulfites and acidic sulfates are used. Bases used for neutralizing these acids are alkali metals, calcium, ammonium, and/or alkanolamines having not more than 12 carbon atoms.

(e) Water-soluble alkanolamines and aqueous ammonia

The alkanolamines are preferably odorless, and examples are triisopropanolamine and 2-amino-2-methyl-1-propanol.

(f) Mixture of iodine pentoxide and sulfuric acid

Preferably, the mixture contains about 15 to 35% by weight of sulfuric acid.

(g) Water-soluble natural polymers and derivatives thereof

There can be used water-soluble natural polymers which gel upon concentration and/or acidification, such as sodium alginate, gum arabic, pectin, agar, carrageenan (a kind of sea algae), abelmoschus and mannose, and derivatives of these.

(h) Alkali metal hypochlorites

Sodium, potassium and lithium hypochlorites can be used.

One or more of the above additives are selected according to the type of a malodor-causing substance. The amount of the additive varies depending upon the concentration of the malodor-causing substance, but can usually be selected from the range of 1 to 10000 ppm in the deodorant.

When the additives are used alone for deodorizing purposes, they may show a fairly high deodorizing effect on some particular malodor-causing substances, but the effect is still inferior to the case of using them in combination with the water-soluble organic polymers used in this invention. This may be attributed to the following possible reasons.

(1) The additive alone cannot completely deodorize a malodor-causing substance unless it is used in a stoichiometrically excessive amount with respect to the malodor-causing substance. However, when it is used in combination with the organic polymer in accordance with this invention, a complete deodorizing effect can be obtained in many cases by using the additive in a concentration below the stoichiometrical amount. This is presumably because of the flocculating action of the polymer.

(2) Where there are many kinds of complex malodor-causing substances as in putrefying odors of animal materials or animal excretions, the additive alone has a very low deodorizing effect and cannot last long. When a deodorizing liquid having a pH of 3.5 to 4.5 by including DL-malic acid as the additive is used, its deodorizing effect becomes longer lasting presumably because it inhibits the growth of putrefying bacteria on the surface of the malodor-causing substances. The addition of calcium benzoate, calcium ascorbate, calcium gluconate, calcium carbamate, calcium propionate or an alkali metal salt thereof under weak acidity or neutrality brings about a synergistic effect of increasing deodorization of malodors whose main cause is the generation of hydrogen sulfide as in putrefying odors, of materials of the animal origin or animal excretions with longer lasting properties.

(3) When a single additive is used as an aerosol or spray, its scattering particles stay only for a short period of time in air, and upon loss of moisture, settle as crystals or a powder. Thus, unless it is sprayed continuously, its deodorizing effect rapidly disappears. When it is used in combination with the water-soluble organic polymer in accordance with this invention, fine particles of the sprayed deodorant liquid dry gradually in air, and with it, the organic polymer, while being mixed with the additive, is given buoyancy by the evaporation of moisture and thus can stay long in air as porous fine particles having a low density. This is considered to be the reason why the deodorant shows a high deodorizing effect.

The concentration of the water-soluble organic polymer used in this invention is 0.05 to 50 ppm, preferably 0.1 to 20 ppm, most preferably 0.5 to 5 ppm, as solids in the aqueous medium. It is very important to prevent biodegradation of the polymer and to take measures so as to maintain the level of the molecular weight of the polymer. For this purpose, it is desirable to sterilize water for dilution by boiling or the like and to reduce the level of the dissolved oxygen, preferably to zero. Preferably, a preservative or antiseptic is added to the diluting water in a concentration within the range legally stipulated. Examples of the preservative or antiseptic include ethanol, acetone, ethers such as diethyl ether, glyoxal, glycerol, ethylene glycol, polyethylene glycol, polyethylene glycol dimethyl ether, sodium benzoate, alkali salts of sorbic acid, isobutyl p-hydroxybenzoate, isopropyl p-hydroxybenzoate, ethyl p-hydroxybenzoate, sodium dehydroacetate, and a minute amount (not more than 0.01%) of formaldehyde. Furthermore, to prevent inclusion of putrefying bacteria, enzymes and/or decomposing bacteria, it is preferred to control devices used in the dissolution, dilution, mixing, transportation, storing and filling of the polymer and in the deodorizing operation carefully throughout the entire operations.

The deodorizing method using the deodorant of this invention is preferably carried out by spraying the deodorant onto a flowable or nonflowable gas, liquid or solid which has malodors and/or give off malodors by using an aerosol method or by means of a spray gun.

As aerosol propellants, propane gas, butane gas, liquefied natural gas, liquefied petroleum gas, dimethyl ether, and freon gases which are a series of chlorofluoroalkanes sold by E. I. du Pont de Nemours & Co., for example, are sealed into metal containers having a jet nozzle. The spray gun is desirably of the type which can disperse the deodorant into as fine particles as possible, and both airless-type and air-type spray guns may be used.

In another embodiment of the deodorizing method, the deodorant of the invention is impregnated in advance in various forms of solids, for example a powder, fiber, film or porous material is brought into approach to, or contact with, a gas, liquid or solid which gives off malodors to thereby achieve deodorization.

The water-soluble organic polymers used in the deodorant of this invention show a considerable removing effect on malodorous components such as a wider range of toxic gases and offensive odors. This effect is considered to be due to a physical flocculating effect rather than to a chemical reaction. When the water-soluble organic polymers are atomized into toxic gases or malodorous gases or as impregnated or included into a substrate, are contacted with such gases, they efficiently capture the malodorous components physically. However, depending upon the types of the malodorous components, the extent of capturing is low or imperfect or the capturing effect does not last long. By further incorporating the aforesaid additives, the malodorous components can be captured more effectively, namely not only physically but also chemically.

According to the present invention, malodorous components can be efficiently removed by a combination of the physical capturing effect of the water-soluble organic polymers used in this invention and the chemical capturing effect of the additives properly selected according to the purpose of deodorization. Since the malodor-causing substances physically and chemically captured as above become nontoxic solids or a gel-like mixture or composite with the water-soluble organic polymers, they have a high specific gravity and easily settle. In particular, when the deodorant of this invention is used adsorbed on a porous or gel-like substrate, its effect lasts for an extended period of time. It is noteworthy that when a diluted aqueous solution of sodium bicarbonate is sprayed onto HCl gas or a diluted aqueous solution of sodium sulfite is sprayed onto $SO_2$ gas to remove these gases in the form of NaCl or $NaHSO_3$ respectively, the inclusion of about 5 ppm of the aforesaid water-soluble organic polymer (for example, polyacrylamide having a number average molecular weight of about 8,000,000) in the diluted aqueous solution can surprisingly lead to the same or higher level of removal ratio even if the concentration of sodium bicarbonate or sodium sulfite is lowered to $\frac{1}{3}$ to 1/5 of its amount actually reacted. The present inventors have confirmed from many examples that the efficiency of capturing malodorous components depends 60 to 80% upon physical capturing by the flocculation of the water-soluble organic polymer, and 20 to 40% upon the chemical capturing by the additive.

The deodorant of this invention has a higher deodorizing effect than known deodorants containing polyacrylamide or poly(sodium acrylate). The reasons may be ascribed to the following.

(1) When there are many kinds of malodor-causing substances, deodorants containing a (co)polymer of (meth)acrylamide or sodium (meth)acrylate or a mixture thereof do not show a sufficient effect on some kinds of the malodor-causing substances. With the deodorant of this invention, affinity between the polymer and the malodor-causing substance can be increased, and thus the deodorizing effect can be increased, by making the charge of the polymer suitable for the malodor-causing substance. Since the polymers used in the deodorant of this invention are cationic, weakly anionic or amphoteric, it can be applied to a broad range of substances which give off malodors.

(2) The effect of the deodorant of this invention is considered to be attributed to the physical flocculating effect to a greater extent than to the chemical reaction of the malodor-causing substance and the polymer as an active component of the deodorant. When the deodorant is atomized toward a malodorous gas, the fine particles of the deodorant are afloat for a relatively long period of time since the concentration of the polymer is low and the size of the deodorant is fine. In addition, the buoyancy of the fine particles of the deodorant is promoted by evaporation of moisture, and the fine particles of the deodorant are kept in contact with the malodor-causing substance for a long time to adsorb on it and/or occlude it. This is presumably the reason for the good deodorizing action of the deodorant of this invention. Probably, the flocculation of the polymer occurs at this time.

When the deodorant of this invention makes contact with the malodor-causing substance and has captured it, the flocculating power of the polymer is larger than in the deodorant containing poly(meth)acrylamide or (meth)acrylamide/sodium acrylate copolymer. Hence, the deodorant of this invention can exhibit higher deodorizing effect.

The range of malodor-causing substances which can be deodorized by the deodorizing agent of this invention depend greatly upon the electrical charge of the polymer. Those containing amphoteric polymers are most versatile and have a higher deodorizing effect than those containing nonionic polymers. Cationic or anionic polymers may have suitable deodorizing effects for some kinds of malodor-causing substances. Weakly cationic or weakly anionic polymers often give deodorants of higher performance than strongly cationic or anionic polymers.

The deodorant of this invention can exhibit a deodorizing effect on gases, liquids and solids which give off odors, particularly malodors, and can be used in various applications. Examples of the application include removal of tobacco smell, smells of toilets, and offensive odors of garbage; removal of malodors in vehicles such as automobiles, buses, aircraft, trains and ships and air-conditioned buildings such as hospitals, precision factories and warehouses; removal of malodors in swinery, a cattle raising farm, a chicken farm, a livestock product processing factory and a marine product processing factory; removal of toxic substances or malodors such as formaldehyde, amines, hydrogen sulfide, mercaptans, phenol, ozone and $NO_x$ dissipated into the air from factories producing plastic products, rubber products, pulp and paper, rayon, cellophane and fibers, a printing factory, a painting factory, a steel-making factory, a foundry, and automobiles; removal of body odors from fibrous household article such as blankets, sheets, carpets, shirts and diapers; removal of malodors in refrigerators, houses and offices; inhibition of malodors from wet-type duplicating machines; and removal of the smell of paper money.

Table 2 summarizes typical embodiments of the present invention. In the table the following abbreviations were used in regard to the ionic properties of the water-soluble organic polymers used as essential components and the method of application.

N: nonionic
C: cationic
A: anionic
AM: amphoteric
SP: spraying by a spray gun
AS: use of an aerosol containing a propellant gas
ST: dropwise addition to a gaseous stream
SC: spraying of an aqueous solution of a gas removing agent, or sprinkling of a powder treated with this solution
PW: a solid first treated with an aqueous gas removing agent and then it is used as such or as a mixture with another solid
PR: addition or impregnation to or in a filter, paper, fabrics, felts, etc. by spraying or beating
GL: included into a powder or a gel-like substrate

TABLE 2

| Embodiment | Additive | Form of ionic property of the organic polymer | Main methods of application | Malodorous components to be controlled |
|---|---|---|---|---|
| I | At least one of acids and salts thereof in (a) and (b), oxoacid salts of sulfur in (d), ferrous salt of (f), and (g) | N, C and/or AM | SP, AS, ST, SC, PW, PR or GL | Malodors released by putrefaction and fermentation of living bodies, corpses, secretions and excretions of humans and animals and plants, amine smell, ammonia smell, mercaptans, indoles, skatole, aldehydes, hydrogen sulfide smell and formaldehyde smell |
| II | At least one of (a), (b), ammonium (bi)-carbonate in (c), sulfites and acid sulfites in (d), and (g) | N, C, A (only the ammonium salt) and/or AM | SP, AS, ST, PR or AM | Mixed formaldehyde/amine odors evolved from formaldehyde, urea resins and melamine resins |
| III | Compounds in (a), (b) and (c) other than the (bi) carbonates and ammonium salts, the com- | N, C, A or M. | SP, AS, ST, SC, PR | Hydrogen halides |

TABLE 2-continued

| Embodiment | Additive | Form of ionic property of the organic polymer | Main methods of application | Malodorous components to be controlled |
|---|---|---|---|---|
| | pounds (d) other than the alkali metal salts, and (e) | | | |
| IV | Sulfites in (d) | N, C, A and/or AM | SP, AS, ST, PW, PR | $SO_2$ gas (example: $SO_2 + Na_2SO_3 + H_2O = 2NaHSO_3$) |
| V | Carbonates in (c) | N, C, A and/or AM | SP, AS, ST, PW, PR | $SO_2$ gas (example: $SO_2 + (NH_4)_2SO_3 + H_2O = 2NH_4HSO_3$) |
| VI | (c), (e) and (f) | N, C, A and/or AM | SP, AS, ST, PW, PR | $H_2S$, mercaptans, alkyl sulfides |
| VII | Sulfites and thiosulfates in (d) | N, C, A and/or AM | SP, AS, ST, PW, PR | $NO_2$ gas |
| VIII | (g) agar | C and/or AM | SP, AS, ST | Heat decomposition gases of phenolic resins |
| IX | Thiosulfates in (d) | N, C, A and/or AM | SP, AS, ST, PW, PR | HCN and other cyanide gases |
| X | (h) | A (nitrogen-free) | SP, AS, ST, PW, PR | HCN and other cyanide gases |
| XI | (c) and (e) | N, C, A and/or AM | SP, AS, ST, PW, PR | Halogen gases |

(Note):
The letters (a) to (h) given in the column of Additive are those given hereinabove.

The following Examples and Referential Examples illustrate the present invention more specifically. In these examples, percentages given are by weight (except for percent decreases).

EXAMPLES 1 TO 8 AND REFERENTIAL EXAMPLES 1 to 7

An aqueous solution (150 ml) was prepared by dissolving each of the water-soluble organic polymers shown in Table 3 and ethyl alcohol uniformly in aseptic water having no dissolved oxygen so that the solids concentration of the polymer was 0.0001% (1 ppm) and the content of ethyl alcohol was 3.3%. The aqueous solution was put into an aluminum container having a capacity of 230 ml and equipped with a spray nozzle. Dimethyl ether (about 80 ml) was sealed into the container to prepare an aerosol deodorant.

Each of the malodor-causing substances indicated in Table 4 was filled in a closable cubic rectangular chamber of non-permeable polyethylene film each side measuring 1 m and having a height of 2 m. At a site 30 cm below the center of the ceiling of this chamber, the above aerosol was sprayed out twice for 2 seconds downwardly. After standing for 60 seconds, the percent decrease of the malodor-causing substance from its amount before the aerosol application was determined, and the results are shown in Table 4.

TABLE 3

| Polymer designation | Monomer composition (%) of (co)polymer | Number average molecular weight | Ionic property |
|---|---|---|---|
| A | Acrylamide (100) | about 6,000,000 | Nonionic |
| B | Sodium acrylate (100) | about 6,000,000 | Anionic |
| C | Ammonium acrylate (100) | about 6,000,000 | Anionic |
| D | Dimethylaminoethyl acrylate (100) | about 6,000,000 | Cationic |
| E | Acrylamide/dimethylaminoethyl-methacrylate (50/50) | about 400,000 | Cationic |
| F | Acrylamide/vinylsulfonic acid/dimethylamino-N—methylmethacrylamide (70/10/20) | about 400,000 | Amphoteric |
| G | Acrylamide/vinylbenzenesulfonic acid/dimethylaminoethyl acrylate (85/5/10) | about 350,000 | Amphoteric |

(Note):
Polymers C to G are used in this invention, and the other polymers are for comparison.

TABLE 4

| Example (Ex.) or Referential Example (REx.) | Polymer used | Malodor-causing substance | Measuring method | Before spraying (ppm) | After spraying (ppm) | Percent decrease (%) |
|---|---|---|---|---|---|---|
| REx. 1 | A | Trimethylamine | Gas-chromatography | 88 | 39 | 55.7 |
| REx. 2 | B | " | Gas-chromatography | 82 | 67 | 18.3 |
| REx. 3 | A | Hydrogen sulfide | Gas-chromatography | 45 | 18 | 60.0 |
| REx. 4 | B | Methylmercaptan | Gas-chromatography | 10 | 6 | 60.0 |
| REx. 5 | B | Ethyl acrylate | Gas-chromatography | 23 | 20 | 13.0 |
| REx. 6 | A | Phenol | Gas-chromatography | 31 | 8 | 74.2 |

TABLE 4-continued

| Example (Ex.) or Referential Example (REx.) | Polymer used | Malodor-causing substance | Measuring method | Before spraying (ppm) | After spraying (ppm) | Percent decrease (%) |
|---|---|---|---|---|---|---|
| REx. 7 | B | " | Gas-chromatography | 28 | 16 | 42.9 |
| Ex. 1 | C | Trimethylamine | Gas-chromatography | 87 | 5 | 94.3 |
| Ex. 2 | D | " | Gas-chromatography | 92 | 14 | 84.8 |
| Ex. 3 | C | Hydrogen sulfide | Gas-chromatography | 43 | 4 | 90.7 |
| Ex. 4 | G | Methylmercaptan | Gas-chromatography | 12 | 2 | 83.3 |
| Ex. 5 | C | Ethyl acrylate | Gas-chromatography | 28 | 4 | 85.7 |
| Ex. 6 | D | Phenol | Gas-chromatography | 33 | 0 | 100 |
| Ex. 7 | E | " | Gas-chromatography | 29 | 2 | 93.1 |
| Ex. 8 | F | " | Gas-chromatography | 27 | 0 | 100 |

EXAMPLE 9 AND REFERENTIAL EXAMPLES 8 AND 9

In the same test chamber as used in Examples 1 to 8, a thick cigar (ROMEO Y JULIETA made by Havana Cuba) was lit and smoked 10 times by a person having a breathing capacity of about 3,000 for 3 minutes to fill the chamber with the smoke. An aerosol deodorant having the polymer G used in Example 4 (Example 9) was sprayed for 2 seconds three times in the chamber. Thereafter, three non-smoking persons were caused to smell the remaining odor. It was recognized that the smell of the cigar was nearly completely removed.

On the other hand, an aerosol deodorant containing polymer A used in Referential Example 1 (Referential Example 8) and an aerosol containing the polymer B used in Referential Example 2 (Referential Example 9) were not so effective in the same test, and marked remaining of the cigar smell was perceived.

EXAMPLES 10 AND 11 AND REFERENTIAL EXAMPLES 10 and 11

A deodorant having each of the compositions shown in Table 5 was sprayed by a spray gun into an exhaust opening in a foundry at a rate of 100 ml/m³ of exhaust gas per minute. This foundry had a large amount of peculiar malodors discharged during the casting of metals using shell molds produced by using granular phenolic resin (FOUNDREZ TD-3430-B of Dainippon Ink and Chemicals, Inc.). The results are shown in Table 5.

TABLE 5

| Deodorant recipe | Example 10 | Example 11 | Referential Example 10 | Referential Example 11 |
|---|---|---|---|---|
| Polymer used (1 ppm) | Polymer E | Polymer F | Polymer A | Polymer B |
| Polyethylene glycol (PEG) nonylphenol ether (PEG 40 moles) | 10 ppm | 10 ppm | 10 ppm | 10 ppm |
| Deodorizing effect | Great | Great | None | None |

EXAMPLE 12

A deodorant solution containing 5 ppm of a copolymer of acrylamide/ammonium acrylate (weight ratio of 60/40 and having a number average molecular weight of 7,500,000, 200 ppm of glycerol and 5 ppm of sodium dehydroxyacetate was supplied intermittently to a filter made of a nonwoven fabric for use in centralized heating and air ventilation in buildings. Thus, while wetting the filter in this way, ventilation was carried out. It was confirmed that odors from curing rooms, odors from lavatories, tobacco smells and offensive odors from outside could be efficiently removed, and clear and fresh feelings could be given to people within the buildings.

EXAMPLE 13

In chemical plants handling various chemicals and in sewage in districts where houses and factories existed together, odors were given off when piling up sludges on the ground or transporting them. To remove such odors, an aqueous solution containing 10 ppm of the polymer of Example 7 was sprayed in liquid form onto the surface of the sludges or by a spray gun at a rate of less than 100 ml/m². It was confirmed that unless the rain washed it off, the deodorant aqueous solution remained effective for several days.

EXAMPLES 14 AND 15 AND REFERENTIAL EXAMPLES 12 AND 13

Wool blankets were immersed in each of the deodorants shown below, squeezed by a centrifugal dehydrator to a pick-up of about 85%, dried completely to a constant weight, and continuously used without washing by three boys aged 18, 20 and 22 having strong body odors for ten days during sleeping at night. The state of adsorption of the body odors to the blankets was then evaluated by three women aged 28, 36 and 49, respectively, having a keen sense of smell. The results are shown below.

| Deodorant recipe | Example 14 | Example 15 | Referential Example 12 | Referential Example 13 |
|---|---|---|---|---|
| Polymer used (20 ppm) | Polymer C | Polymer G | Polymer B | Blank |
| Sodium dehydroacetate | 20 ppm | 20 ppm | 20 ppm | 20 ppm |
| State of odor | +− | − | + | ++ |

| Deodorant recipe | Example 14 | Example 15 | Referential Example 12 | Referential Example 13 |
|---|---|---|---|---|
| adsorption | | | | |

(Note):
++: Strong odor
+: Considerable odor
+−: Some odor
−: Slight odors
−−: No odors

EXAMPLE 16 AND REFERENTIAL EXAMPLE 14

An acrylamide/ammonium acrylate (60/40) copolymer having a number average molecular weight of about 8,500,000 was added to a solution containing 20% of neutral sodium sulfate as $Na_2SO_4$. The solution was concentrated and taken out in the form of crystals of $Na_2SO_4 \cdot 10H_2O$. Sodium sulfate crystals containing a small amount of the water-soluble polymer showed an excellent deodorizing effect as a deodorant for application to dip-up type toilets, animal carcasses, garbage, and the like.

On the other hand, the application of $Na_2SO_4 \cdot 10H_2O$ alone did not show a sufficient deodorizing effect.

EXAMPLE 17

Water containing 18 ppm of the polymer of Example 16 was added to 0.05 g of sodium sorbate to form a mixture having a weight of 100 g. The mixture was heated and uniformly dissolved. Then, the solution was cooled to room temperature and put in a mold having a size of 4 cm×5 cm×5 cm to gel it. When the resulting gel was put in a cloth bag and used in refrigerators and inside automobiles as a deodorant, it showed an excellent deodorizing effect.

EXAMPLES 18 TO 33 AND REFERENTIAL EXAMPLES 15 TO 22

A mixture of (96.7−x) parts by weight of each of the polymers shown in Table 6 as a 0.0002% (2 ppm) solution, 3.3 parts by weight of ethanol and x parts by weight of each of the additives indicated in Table 7 was uniformly dissolved in aseptic water containing no dissolved oxygen to prepare an aqueous solution. Each of the various malodorous substances shown in Table 7 was filled in a cubic closed chamber surrounded by non-permeable polyethylene film each side measuring 1 m and having a height of 2 m. The aqueous solution was sprayed by an air spray gun at a site 30 cm below the center of the ceiling of the chamber twice for 2 seconds in a total amount of 36 ml. After standing for 60 minutes, the percent decrease of the toxic gas from its amount before the spraying was measured, and the results are shown in Table 7.

TABLE 6

| Polymer designation | Monomer composition (by weight) of the (co)polymer | Number average molecular weight | Ionic property |
|---|---|---|---|
| N | 100% Acrylamide | about 9,000,000 | Nonionic |
| A | Acrylamide/ammonium acrylate (60/40) | about 4,500,000 | Anionic |
| C | Dimethylaminoethyl methacrylate/acrylamide (30/70) | about 6,000,000 | Cationic |
| AM | Acrylamide/vinyl sulfonic acid/dimethylaminoethyl acrylate (80/10/10) | about 3,000,000 | Amphoteric |

The concentration of the gas was measured by using a Kitagawa-type gas detector (KITAGAWA PRECISION GAS DETECTOR).

$$\text{Percent decrease} = \frac{\left(\begin{array}{c}\text{Concentration}\\\text{before spraying}\\\text{(ppm)}\end{array}\right) - \left(\begin{array}{c}\text{Concentration}\\\text{after spraying}\\\text{(ppm)}\end{array}\right)}{\text{Concentration before spraying (ppm)}} \times 100$$

The concentration of the additive shows the weight percent based on the solution.

TABLE 7

| Example (Ex.) or Referential Example (REx.) | Polymer used | Additive and its amount | | Malodorous substance | Before spraying (ppm) | After spraying (ppm) | Percent decrease (%) |
|---|---|---|---|---|---|---|---|
| REx. 15 | N | None | | Formaldehyde | 29 | 7 | 76 |
| Ex. 18 | N | Ammonium carbonate | 0.5% | " | 31 | 3 | 90 |
| Ex. 19 | N | " | 1.0% | " | 28 | 1 | 96 |
| Ex. 20 | A | " | 0.5% | " | 32 | 0 | 100 |
| REx. 16 | C | None | | Sulfurous acid gas | 22 | 6 | 73 |
| Ex. 21 | C | Sodium sulfite | 0.3% | " | 28 | 1 | 96 |
| Ex. 22 | C | Ammonium sulfite | 0.3% | " | 28 | 1 | 96 |
| REx. 17 | A | None | | Hydrogen sulfide | 20 | 16 | 20 |
| Ex. 23 | A | Triisopropanolamine | 0.3% | " | 22 | 1 | 95 |
| Ex. 24 | A | Sodium bicarbonate | 1.0% | " | 18 | 0 | 100 |
| REx. 18 | N | None | | Hydrogen cyanide | 63 | 18 | 71 |
| Ex. 25 | N | Sodium thiosulfate | 0.3% | " | 78 | 2 | 97 |
| Ex. 26 | N | " | 1.0% | " | 60 | 0 | 100 |
| REx. 19 | N | None | | Carbon monoxide | 256 | 214 | 16 |
| Ex. 27 | N | Iodine pentoxide | 2.0% | " | 277 | 40 | 86 |
| | | Sulfuric acid | 0.5% | | | | |
| REx. 20 | N | None | | Hydrogen chloride | 33 | 8 | 76 |
| Ex. 28 | N | Sodium bicarbonate | 0.3% | " | 37 | 0 | 100 |
| Ex. 29 | A | " | | " | 36 | 0 | 100 |
| Ex. 30 | AM | " | | " | 33 | 0 | 100 |
| REx. 21 | A | None | | Bromine gas | 12 | 2 | 83 |
| Ex. 31 | A | Sodium bicarbonate | 0.5% | " | 16 | 0 | 100 |
| REx. 22 | N | None | | Nitrogen dioxide | 351 | 38 | 89 |
| Ex. 32 | N | Sodium sulfite | 0.3% | " | 376 | 10 | 97 |

TABLE 7-continued

| Example (Ex.) or Referential Example (REx.) | Polymer used | Additive and its amount | Malodorous substance | Before spraying (ppm) | After spraying (ppm) | Percent decrease (%) |
| --- | --- | --- | --- | --- | --- | --- |
| Ex. 33 | N | "         0.5% | " | 333 | 2 | 99 |

EXAMPLE 34 AND REFERENTAL EXAMPLES 23 and 24

Ethanol (5 ml) and 1.5 g of DL-malic acid were added to an aqueous solution containing 0.5 ppm as solids of the polymer N shown in Table 6 to prepare 150 ml of a solution. The solution was filled in an aluminum can having a 230 ml spray-nozzle, and about 80 ml of dimethyl ether was sealed into the can to prepare an aerosol can (Example 34).

Separately, an aerosol can was prepared as above except that DL-malic acid was not added (Referential Example 23).

The aerosol deodorant was jetted out onto the entire surface of each of the test substances shown in Table 8 at a site about 10 cm apart from it, and thereafter, the degree of malodors was evaluated. The results are shown in Table 8.

TABLE 8

| Test substance | Example 34 | Referential Example 23 | Referential Example 24 (no spray) |
| --- | --- | --- | --- |
| (1) 1 kg of fresh feces of swine | | | + |
| Smell immediately after spraying | — — | — — | + |
| Smell after 3 days (25° C.) | — | + | + + |
| (2) 500 g of mackerel entrails | | | + |
| Smell immediately after spraying | — — | — — | + |
| Smell after 3 days (25° C.) | — | + | + + |
| (3) 500 ml of sewer sludge containing 10% of soybean meal | | | + |
| Smell immediately after spraying | — — | — — | + |
| Smell after 10 days (25° C.) | — | + | + + |

The odors were evaluated by a panel of five persons having a normal sense of smell, a 22 year-old male, a 30-year old male, a 31 year-old male, a 52 year-old female and a 68-year old male on the basis of the following five grades. Both extremities were excluded from the resulting evaluation data, and the remaining three data were averaged, and shown in Table 8.

++: very unpleasant smell of putrefaction +: considerably strong smell of putrefaction +−: some smell of putrefaction −: slight smell of putrefaction − −: no smell of putrefaction

EXAMPLE 35

A wood fire retardant which contained 190 g of 3-(dimethylphosphono)propionamide, 400 g of methylated hexamethylolmelamine, 10 g of nonyl phenol ethylene oxide (40 moles) adduct, 1 g of a defoamer (NOPCO NDW, a product of Sunnopco Co.) and 24 g of hydrogen chloride per kg, was water-soluble at room temperature-curable and had a pH of 2.1 and a free formaldehyde content of 0.9% was sprayed onto the surface of a wood by an airless spray gun. At the same time, the deodorant of Example 20 was lightly blown into air in front of the operator and above the operator. The operator was caused to wear a protective respiration mask on all over his face (ULTRATWIN RESPIRATOR sold by MSA Japan Co., Ltd.; a nonwoven fabric impregnated with a mixture of the aqueous solution of Example 1 and 0.2% of sodium bicarbonate was used in a respiration cartridge), and allowed to perform the operation for about 1 hour. The operator did not at all feel irritation to the mucosa of the eyes or the nose by formaldehyde or the acidic treating liquor during the operation. The amount of hydrogen chloride and formaldehyde detected in the gas taken from inside the mask by means of a gas detecting tube were zero. Thus, irritant gases were completely prevented from dissipating into the air around the working environment.

EXAMPLE 36 AND REFERENTIAL EXAMPLE 25

Two plywoods of Siebold's beech having a thickness of 5.5 mm and coated with the treating liquors of Example 35 at a rate of about 200 g/m$^2$ were left to stand horizontally for 24 hours at 25° C. to gel the treating liquor. A solution prepared by adding 0.05% of sodium dehydroacetate was added to the solution of Example 18 was coated on the surface of one of the plywoods at a rate of 60 g/m$^2$ (Example 36). The other plywood (Referential Example 25) was left untreated. The two plywoods were each put in a desiccator at 25° C. and 65% RH (no moisture controlling agent), and left to stand for 48 hours. Then, the rubber stopper was pulled from the desiccator, and the amount of free formaldehyde was measured. It was 0 ppm in Example 36, but 12 ppm in Referential Example 25.

EXAMPLES 37 TO 39 AND REFERENTIAL EXAMPLES 26 AND 27

An aqueous solution was prepared which contained 0.05 g of tartaric acid (Example 37), citric acid (Example 38) or succinic acid (Example 39), 0.05% of sodium sorbate and 20 ppm of the water-soluble polymer N of Example 18. Furthermore, an aqueous solution containing only the water-soluble polymer N (Referential Example 26) was prepared. Each of the aqueous solutions was impregnated into a cloth for diapers, and dried.

Separately, a non-treated cloth was used in Referential Example 27.

Ten milliliters of human urine was dropped onto the central part of the cloth by a measuring pipette, and the cloth was put into a polyethylene bag. The bag was closed, and left to stand at 30° C. Changes in odor were examined. The results are shown in Table 9.

TABLE 9

| | Example 37 | Example 38 | Example 39 | Ref Ex. 26 | Ref. Ex. 27 |
| --- | --- | --- | --- | --- | --- |
| Immediately after | — | — | — | — | +− |

TABLE 9-continued

|  | Example 37 | Example 38 | Example 39 | Ref Ex. 26 | Ref. Ex. 27 |
|---|---|---|---|---|---|
| 6 hours later | − | − | − | +− | + |
| 12 hours later | − | − | +− | + | ++ |

(Note)
−: hardly any odor
+: considerable odor
+−: slight odor
++: strong odor

EXAMPLES 40 TO 50 AND REFERENTIAL EXAMPLES 28 TO 31

The following four water-soluble organic polymers having different monomer compositions or different substituents were prepared.

| No. | Ionic property | Monomer composition (moles) or substituent |
|---|---|---|
| H | Nonionic | Polymer composed only of acrylamide |
| I | Anionic | Acrylamide/sodium acrylate (85/15) copolymer |
| J | Cationic | Polymer of acrylamide in which 20% of the amide groups were converted to dimethylamino-N—methylacrylamide groups by the Mannich reaction (nonionic/cationic mole ratio 80/20) |
| K | Amphoteric | Polymer No. I in which 20% of the 85 mole % amide groups were converted to dimethylamino-N—methylacrylamide groups as in polymer J (nonionic/anionic/cationic mole ratio 65/15/20) |

Since the cationic and amphoteric polymers contained formaldehyde, dimethylamine and acrylamide, and the nonionic and anionic polymers contained acrylamide, these polymers were each well washed with pure ethanol, and dried at low temperatures. The dried polymers were then dissolved in boiling deionized water to prepare 0.1% (1000 ppm) aqueous solutions. These polymers had a number average molecular weight of about 8,000,000.

By using these aqueous solutions, a series of deodorizing tests shown in Table 10 were carried out.

The methods of measuring the concentration of the gas and the percent decrease were the same as in Examples 18 to 33.

The concentration of the polymer in the deodorant solution was 5 ppm as solids, and the concentration of ethanol in it was 4% by weight.

TABLE 10

| Ex. or REx. | Polymer used (5 ppm as solids) | Additive and its amount | Substance to be removed | Before jetting (ppm) | After jetting (ppm) | Percent decrease (%) |
|---|---|---|---|---|---|---|
| REx. 28 | H (nonionic) | None | Hydrogen chloride | 25 | 8 | 68 |
| Ex. 40 | H (nonionic) | Calcium benzoate (0.05) | " | 22 | 2 | 91 |
| Ex. 41 | H (nonionic) | Calcium gluconate (0.05) | " | 26 | 1 | 96 |
| REx. 29 | I (anionic) | None | Ethyl mercaptan | 5 | 3 | 40 |
| Ex. 42 | I (anionic) | Sodium hypochlorite (0.01) | " | 5 (detection limit 1) | below 1 (detection limit 1) | above 80 |
| REx. 30 | I (cationic) | None | Hydrogen sulfide | 25 | 6 | 76 |
| Ex. 43 | J (cationic) | Sodium alginate (20 ppm) | " | 28 | 2 | 93 |
| Ex. 44 | Polymer prepared by adding DL-malic acid to J (cationic) to adjust its pH to 2.5, converting it into a quaternary ammonium salt, and then diluting the product with water (the 5 ppm solution had a pH of 6.0) | L-malic acid mentioned in the left column | " | 24 | 3 | 88 |
| REx. 31 | K (amphoteric) | None | Sulfurous acid gas | 45 | 12 | 73 |
| Ex. 45 | K (amphoteric) | Calcium pantothenate (0.1) | " | 48 | 6 | 88 |
| Ex. 46 | K (amphoteric) | Sodium sulfite (20 ppm) | " | 42 | 2 | 95 |
| Ex. 47 | K (amphoteric) | Calcium lactate (0.2) | " | 46 | 4 | 91 |
| Ex. 48 | Polymer obtained by adding DL-malic acid to K (amphoteric) to adjust its pH to 2.0, converting it into a quaternary ammonium salt, and then diluting the product with water (the 5 ppm solution had a pH of 4.5) | None | " | 42 | 3 | 93 |
| Ex. 49 | same as in Ex. 48 | Sodium bicarbonate was added to adjust pH to 6.8 | " | 46 | below 1 | above 98 |
| Ex. 50 | same as in Ex. 49 | Sodium alginate (20 ppm) | " | 40 | below 1 | above 98 |

EXAMPLES 51 TO 53 AND REFERENTIAL EXAMPLE 32

The polymers I, J and K shown in Table 10 were tested for deodorizing effects on offensive odors generated incessantly from a patient with a cancer in the last stage hospitalized in a hospital in Tokyo and an old man requiring incessant care of the family because of a loss of free activity. The test was carried out for about 2 months by the cooperation of physicians and nurses of the hospital and the family of the patient.

Deodorizing testing methods (1) An aerosol comprising a mixture of 65% by weight of an aqueous solution containing 3.5 ppm of each of the polymers, 4% of ethanol and an additive and 35% by weight of dimethyl ether was sealed into a corrosion-resistant metallic can. The aerosol was sprayed intermittently into a room evolving offensive odors for several seconds each time.

(2) An aqueous solution containing about 10 ppm of each of the polymers and an additive was put into a receptable containing dirts or excretions.

(3) Each of the polymers was added to a concentration of 5 to 10 ppm to rinsing water for washing apparel.

(4) The solution mentioned in (2) above was impregnated into a large bath towel and lightly dehydrated. The bath towel was then suspended in a room evolving offensive odors.

Formulations and test results

Referential Example 32

In the case of using only the anionic polymer I, a fairly good result was obtained by any of the testing methods (1), (2), (3) and (4), but the offensive odors could not completely be removed.

EXAMPLE 51

The polymer J made weakly acidic by addition of DL-malic acid had slightly improved deodorizing properties over Referential Example 32 by any of these testing methods.

EXAMPLE 52

When as in Example 49, the polymer was converted to a quaternary ammonium salt and then neutralized with sodium bicarbonate, the deodorant showed an improvement in deodorizing effect over Referential Example 32. The durability of the deodorizing effect was also observed.

EXAMPLE 53

A deodorant solution obtained by adding 0.05% of calcium benzoate to 3.5 ppm of the amphoteric polymer K shows a particularly superior effect of removing the offensive odors to that in Referential Example 32 by any of the testing methods (1), (2), (3) and (4).

EXAMPLE 54 AND REFERENTIAL EXAMPLES 33 AND 34

Equimolar proportions of formaldehyde and dimethylamine were added to an aqueous solution of an anionic copolymer of acrylamide/acrylic acid (weight ratio 85/15) having a number average molecular weight of about 8,000,000. They were reacted to prepare an aqueous solution containing 10% as solids of an amphoteric polymer of acrylamide/acrylic acid/dimethylamino-N-methylacrylamide (weight ratio 70/15/15). A large amount of methanol was added to the aqueous solution to coagulate the polymer. The mixture was filtered, well washed with methanol, and dried to a constant weight with air at 40° C. The dried product was washed with pure ethanol to remove the unreacted materials. The amounts of the toxic unreacted materials contained in a 0.1% aqueous solution of this polymer were as follows:

Formaldehyde: less than 5 ppm (the absorbance method using acetylacetone; detection limit 5 ppm)

Acrylamide: not detected (gas chromatographic method; detection limit 10 ppm)

Dimethylamine: not detected (high-performance chromatographic method; detection limit 5 ppm)

The 0.1% aqueous solution was tested for LC50 (median lethal concentration) on killi-fish by the method set forth in JIS K-0102. In the 24-hour test, the LC50 was more than 50,000 ppm, and in the 48-hour test, it was 17,500 ppm.

Aluminum aerosol cans containing 65 parts by weight of 4.0 ppm as solids of the 0.1% aqueous solution mentioned above and 4% of pure ethanol (Example 54), aluminum aerosol cans prepared as above using polyacrylamide having a number average molecular weight of about 8,000,000 (Referential Example 33) and aluminum aerosol cans prepared as above using acrylamide/sodium acrylate (50/50 by weight) copolymer having a number average molecular weight of 8,000,000 were handed to 7 monitors (2 for each), and they were requested to perform a deodorizing test on malodors such as a fecal smell, household garbage, tobacco smokes and body odors on apparels. As a result of the tests, all agreed in evaluation as follows:

First place: Example 54 (the deodorizing effect was particularly good)

Second place: Referential Example 33 (the deodorizing effect was good, but inferior to Example 54)

Third place: Referential Example 34 (no significant deodorizing effect)

EXAMPLE 55

The 0.1 aqueous solution of the polymer used in Example 54 was sprayed in a concentration of 1 ppm to 10 ppm as solids on entrails of animals or fish or putrefied products thereof. The offensive odors could be markedly reduced.

EXAMPLE 56

The polymer used in Example 55 was adjusted to pH 2.5 with citric acid and converted to a quaternary ammonium salt. The quaternary ammonium salt type of the polymer was then used as in Example 55. The deodorizing effect increased considerably and its durability also increased. This is presumably because the putrefaction was prevented by the acid, and ammonia and alkylamines generated were neutralized with the acid.

What is claimed is:

1. A deodorant comprising (I) as an active deodorizing agent, a water soluble organic polymer containing at least one group selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts; (c) cationic groups and, (d) a quaternized ammonium group; or a mixture of such water-soluble organic polymers, and (II) an aqueous medium; wherein the water-soluble organic polymer and its quaternary ammonium compound has a number average molecular weight of at least 1,000,000 and wherein the concentration of the water-soluble organic polymer, its quaternary ammonium compound or mixture thereof is 0.05 to 50 ppm as solids.

2. A method of deodorization, which comprises spraying a deodorant comprising (I) as an active deodorizing ingredient, a water-soluble organic polymer having a number average molecular weight of at least 1,000,000 and containing at least one group selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group, and their alkali metal salts, ammonium salts, alkanolamine salts and alkali metal/ammonium/alkanolamine mixed salts; (c) cationic groups and, (d) a quaternized ammonium group; or a mixture of such water-soluble organic polymers, and (II) an aqueous medium into a flowable or non-flowable gas,
  spraying it to the surface of a solid,
  impregnating it into a porous metal, or
  incorporating it into a powder or a gel-like substrate.

3. A deodorant in the form of an aerosol spray composition comprising (I) as an active deodorizing agent, a water soluble organic polymer containing at least one group selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts; (c) cationic groups and, (d) a quaternized ammonium group; or a mixture of such water-soluble organic polymers, and (II) an aqueous medium; wherein the water-soluble organic polymer and its quaternary ammonium compound has a number average molecular weight of at least 1,000,000, and which further comprises an aerosol propellant.

4. A deodorant comprising (I) as an active deodorizing agent, a water soluble organic polymer containing at least one group selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts; (c) cationic groups and, (d) a quaternized ammonium group; or a mixture of such water-soluble organic polymers, and (II) an aqueous medium; wherein the water-soluble organic polymer and its quaternary ammonium compound has a number average molecular weight of at least 1,000,000, impregnated in a porous material.

5. A deodorant comprising (I) as an active deodorizing agent, a water soluble organic polymer containing at least one group selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts; (c) cationic groups and, (d) a quaternized ammonium group; or a mixture of such water-soluble organic polymers, and (II) an aqueous medium; wherein the water-soluble organic polymer and its quaternary ammonium compound has a number average molecular weight of at least 1,000,000, incorporated into a powder or gel-like substrate.

6. A deodorant comprising (I) as an active deodorizing agent, a water-soluble organic cationic polymer, and (II) an aqueous medium; wherein the cationic polymer is selected from the group consisting of poly(dimethylaminoethyl acrylate), copoly(dimethylaminoethyl acrylate/acrylamide), copoly(vinylbenzyl trimethyl ammonium chloride/acrylamide) and copoly(acrylamide/dimethylaminoethyl methacrylate) and has a number average molecular weight of at least 1,000,000.

7. A deodorant comprising (I) as an active deodorizing ingredient, a water-soluble organic amphoteric polymer containing at least two groups selected from the class consisting of (a) ammonium salt of a carboxylic acid group, ammonium/alkali metal mixed salts of a carboxylic acid group and alkanolamine salts of a carboxylic acid group; (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts; and (c) cationic groups, or a mixture of such amphoteric polymers, and (II) an aqueous medium; wherein the water-soluble amphoteric polymer or polymers have a number average molecular weight of at least 1,000,000.

8. The deodorant of claim 7 wherein the amphoteric polymer is selected from the group consisting of copoly-(acrylamide/dimethylaminoethyl methacrylate/vinylsulfonic acid), copoly(acrylamide/dimethylaminoethyl acrylate/styrene sulfonic acid), copoly(acrylamide/vinylsulfonic acid/dimethylamino-N-methylmethacrylamide) and copoly(acrylamide/vinylbenzenesulfonic acid/dimethylaminoethyl acrylate).

9. A deodorant comprising (I) as an active deodorizing ingredient a water-soluble acrylamide type polymer or copolymer having a number average molecular weight of at least 100,000 and containing both an anionic group and a cationic group or their respective quaternary ammonium groups, said anionic group being selected from the class consisting of (a) a carboxyl group and its ammonium salt, alkali metal salts, ammonium/alkali metal mixed salts and alkanolamine salts; and (b) sulfoalkyl groups, a sulfonic acid group, a phosphoric acid group, a phosphonic acid group and their alkali metal salts, ammonium salts, alkanolamine salts and alkali metal/ammonium/alkanolamine mixed salts, and (II) an aqueous medium.

10. The deodorant of claim 9 wherein the water-soluble acrylamide type polymer or copolymer has a number average molecular weight of at least 1,000,000.

11. The deodorant of claim 9 wherein the concentration of the water-soluble acrylamide type polymer or copolymer is 0.05 to 50 ppm as solids.

12. The deodorant of claim 9 wherein the water-soluble acrylamide type polymer or copolymer contains at least 5% by weight of (meth)acrylamide.

13. The deodorant of claim 9 in the form of an aerosol spray composition which further comprises an aerosol repellant.

14. The deodorant of claim 9 impregnated in a porous material.

15. The deodorant of claim 9 incorporated into a powder or gel-like substrate.

16. The deodorant of claim 9 wherein the water-soluble acrylamide type polymer or copolymer is selected from the group consisting of copoly(acrylamidedimethylaminoethyl methacrylate/vinylsulfonic acid), copoly(acrylamidedimethylaminoethyl acrylate/styrene sulfonic acid), copoly(acrylamide/vinylsulfonic acid/dimethylamino-N-methylmethacrylamide) and copoly(acrylamide/vinylbenzenesulfonic acid/dimethylaminoethyl acrylate).

17. The deodorant of claim 9 wherein said anionic group is a carboxyl group or an ammonium salt thereof, an alkali metal salt thereof an ammonium/alkali metal mixed salt thereof or alkanolamine salt thereof.

18. A method of deodorization which comprises spraying a deodorant comprising as essential components (I) a water-soluble acrylamide type polymer or copolymer having a number average molecular weight of at least 100,000 and containing both an anionic group and a cationic group or their respective quaternary ammonium groups, said anionic group being selected from the class consisting of (a) a carboxyl group and its ammonium salt, alkali metal salts, ammonium/alkali metal mixed salts and alkanolamine salts; and (b) sulfoalkyl groups, a sulfonic acid group, a phosphoric acid group, a phosphonic acid group and their alkali metal salts, ammonium salts, alkanolamine salts and alkali metal/ammoniumalkanolamine mixed salts, and (II) an aqueous medium into a flowable or non-flowable gas, spraying it to the surface of a solid or liquid, impregnating it into a porous material, or incorporating it into a powder or a gel-like substrate.

* * * * *

UNITED STATES PATENT AND TRADEMARK OFFICE
CERTIFICATE OF CORRECTION

PATENT NO. : 4,909,986
DATED : March 20, 1990
INVENTOR(S) : NOBUO KOBAYASHI ET AL.

It is certified that error appears in the above-identified patent and that said Letters Patent is hereby corrected as shown below:

On the title page item [73] after "Assignee", delete "Dainippon Ink" and insert --Dainippon Ink And Chemicals, Inc.--.

Col. 26, Claim 8, lines 6 and 7 of the claim, delete "/dimethylamino-N - methylmethacrylamide)" and insert
--/dimethylamino-N-methylmethacrylamide)--.

Signed and Sealed this

Seventeenth Day of March, 1992

Attest:

HARRY F. MANBECK, JR.

Attesting Officer

Commissioner of Patents and Trademarks